(12) United States Patent
Gu et al.

(10) Patent No.: US 9,204,809 B2
(45) Date of Patent: Dec. 8, 2015

(54) BLOOD PRESSURE MEASURING DEVICE AND METHOD OF CALIBRATING THEREOF

(75) Inventors: Wenbo Gu, Hong Kong (CN); Chun Zhang, Hong Kong (CN); Tun Lam, Hong Kong (CN); Lap Wai Lydia Leung, Hong Kong (CN)

(73) Assignee: HONG KONG APPLIED SCIENCE AND TECHNOLOGY RESEARCH INSTITUTE COMPANY LIMITED, Hong Kong (CN)

( * ) Notice: Subject to any disclaimer, the term of this patent is extended or adjusted under 35 U.S.C. 154(b) by 930 days.

(21) Appl. No.: 13/364,297

(22) Filed: Feb. 1, 2012

(65) Prior Publication Data
US 2012/0316448 A1 Dec. 13, 2012

(51) Int. Cl.
*A61B 5/021* (2006.01)
*A61B 5/026* (2006.01)
*A61B 5/00* (2006.01)

(52) U.S. Cl.
CPC ........... *A61B 5/02108* (2013.01); *A61B 5/0261* (2013.01); *A61B 5/0082* (2013.01); *A61B 5/489* (2013.01); *A61B 2560/0223* (2013.01); *A61B 2562/046* (2013.01); *A61B 2562/066* (2013.01)

(58) Field of Classification Search
CPC .... A61B 5/021; A61B 5/022; A61B 5/02416; A61B 5/02422; A61B 5/0261; A61B 2560/0223
USPC .......................................... 600/486, 490–507
See application file for complete search history.

(56) References Cited

U.S. PATENT DOCUMENTS

| | | | |
|---|---|---|---|
| 4,987,900 A | 1/1991 | Eckerle et al. | |
| 5,099,853 A | 3/1992 | Uemura et al. | |
| 6,222,189 B1 * | 4/2001 | Misner et al. | 250/341.1 |
| 6,428,482 B1 * | 8/2002 | Sunagawa et al. | 600/485 |
| 6,475,153 B1 * | 11/2002 | Khair et al. | 600/485 |
| 6,475,155 B2 * | 11/2002 | Ogura et al. | 600/500 |
| 6,632,181 B2 * | 10/2003 | Flaherty et al. | 600/485 |
| 6,740,043 B2 * | 5/2004 | Narimatsu | 600/485 |
| 6,918,879 B2 | 7/2005 | Ting et al. | |
| 6,932,772 B2 * | 8/2005 | Kan | A61B 5/02116 600/485 |
| 6,966,879 B2 * | 11/2005 | Hasegawa et al. | 600/485 |
| 2002/0026121 A1 * | 2/2002 | Kan | A61B 5/02116 600/500 |
| 2003/0149369 A1 * | 8/2003 | Gallant et al. | 600/485 |

(Continued)

FOREIGN PATENT DOCUMENTS

CN 101176661 A 5/2008

*Primary Examiner* — Navin Natnithithadha
*Assistant Examiner* — Meredith Weare
(74) *Attorney, Agent, or Firm* — Eagle IP Limited; Jacqueline C. Lui

(57) ABSTRACT

The present invention is a blood pressure measuring device comprising an optical sensing unit adapted for detecting optical pulses at a plurality of locations on an external surface of a user. The device also comprises a processing unit coupled to the optical sensing unit for determining an optimal location from the plurality of locations based on the detected optical pulses and a pressure sensing unit adapted for detecting a pressure pulse of the user at a location of measurement. The present invention also discloses a method of measuring a blood pressure of a user using a blood pressure measurement device. The advantage of the present invention is that by using an optical sensing unit to locate the artery of the user, or to compensate the misalignment from the artery, the blood pressure is more accurately determined. With the calibration method, the deficient cuff calibration can be waived in certain circumstances.

15 Claims, 11 Drawing Sheets

(56) References Cited

U.S. PATENT DOCUMENTS

| | | |
|---|---|---|
| 2008/0058623 A1 | 3/2008 | Lee et al. |
| 2008/0228089 A1* | 9/2008 | Cho et al. .................... 600/485 |
| 2009/0069698 A1* | 3/2009 | Bae et al. .................... 600/485 |
| 2012/0071768 A1* | 3/2012 | Yamakoshi et al. .......... 600/493 |
| 2014/0364749 A1* | 12/2014 | Varma et al. ................. 600/494 |

* cited by examiner

|   | 1 | 2 | 3 | 4 | 5 |
|---|---|---|---|---|---|
| 1 | 193.7 | 170.3 | 508.0 | 244.7 | 0.0 |
| 2 | 93.1 | 0.0 | 709.7 | 439.1 | 258.7 |
| 3 | 0.0 | 0.0 | 1764.1 | 210.2 | 175.9 |
| 4 | 0.0 | 0.0 | 853.7 | 282.7 | 0.0 |
| 5 | 0.0 | 0.0 | 951.8 | 0.0 | 41.6 |

Fig. 5a

|   | 1 | 2 | 3 | 4 | 5 |
|---|---|---|---|---|---|
| 1 | 0.0 | 568.0 | 981.1 | 263.9 | 0.0 |
| 2 | 0.0 | 0.0 | 941.0 | 152.6 | 0.0 |
| 3 | 0.0 | 229.2 | 894.2 | 287.8 | 94.4 |
| 4 | 0.0 | 0.0 | 702.8 | 521.5 | 0.0 |
| 5 | 0.0 | 290.2 | 652.2 | 100.4 | 0.0 |

Fig. 5b

|   | 1 | 2 | 3 | 4 | 5 |
|---|---|---|---|---|---|
| 1 | 0.0 | 245.0 | 445.0 | 384.1 | 225.3 |
| 2 | 0.0 | 224.0 | 241.9 | 526.4 | 0.0 |
| 3 | 251.2 | 347.0 | 1598.9 | 607.2 | 305.7 |
| 4 | 0.0 | 0.0 | 247.1 | 912.0 | 445.4 |
| 5 | 0.0 | 0.0 | 0.0 | 831.1 | 1190.6 |

Fig. 6a

|   | 1 | 2 | 3 | 4 | 5 |
|---|---|---|---|---|---|
| 1 | 0.0 | 0.0 | 789.8 | 0.0 | 781.1 |
| 2 | 0.0 | 0.0 | 0.0 | 827.6 | 790.0 |
| 3 | 0.0 | 0.0 | 1373.1 | 1336.0 | 576.6 |
| 4 | 0.0 | 0.0 | 0.0 | 778.4 | 464.1 |
| 5 | 0.0 | 0.0 | 751.5 | 1102.5 | 178.5 |

Fig. 6b

|   | 1 | 2 | 3 | 4 | 5 |
|---|---|---|---|---|---|
| 1 | 0.0 | 492.8 | 0.0 | 0.0 | 134.5 |
| 2 | 0.0 | 1339.6 | 81.5 | 0.0 | 145.1 |
| 3 | 286.8 | 373.9 | 1424.1 | 534.5 | 144.1 |
| 4 | 245.3 | 0.0 | 836.5 | 241.6 | 0.0 |
| 5 | 0.0 | 0.0 | 781.1 | 156.7 | 0.0 |

Fig. 6c

|   | 1 | 2 | 3 | 4 | 5 |
|---|---|---|---|---|---|
| 1 | 1281.9 | 1589.6 | 746.5 | 236.6 | 168.0 |
| 2 | 924.3 | 1463.0 | 755.8 | 0.0 | 156.9 |
| 3 | 0.0 | 1051.0 | 1285.5 | 1259.5 | 664.1 |
| 4 | 1335.9 | 0.0 | 1400.2 | 723.1 | 0.0 |
| 5 | 659.8 | 0.0 | 603.1 | 0.0 | 0.0 |

Fig. 6d

|      |      |      |
|------|------|------|
| 0.10 | 0.15 | 0.10 |
| 0.15 |      | 0.15 |
| 0.10 | 0.15 | 0.10 |

Fig. 8a

|      |      |      |
|------|------|------|
| 0.05 | 0.15 | 0.15 |
| 0.10 |      | 0.20 |
| 0.05 | 0.15 | 0.15 |

Fig. 8b

BLOOD PRESSURE MEASURING DEVICE AND METHOD OF CALIBRATING THEREOF

FIELD OF INVENTION

This invention relates to a blood pressure measurement device and in particular to a tonometric blood pressure measurement device.

BACKGROUND OF INVENTION

A tonometric blood pressure measurement devices measures blood pressure by placing a pressure sensor on an artery of a user to sense the pressure pulse and calculate the blood pressure. However, the pressure pulse sensed by conventional devices may not reflect the blood pressure accurately, given that the pressure sensor may not be placed directly over the artery and the external pressure applied may not be optimal. An improved blood pressure measurement device is hence desired to improve the accuracy of the pressure sensor.

SUMMARY OF INVENTION

In the light of the foregoing background, it is an object of the present invention to provide an alternate blood pressure measuring device.

Accordingly, the present invention, in one aspect, is a blood pressure measuring device comprising an optical sensing unit adapted for detecting optical pulses at a plurality of locations on an external surface of a user. The device also comprises a processing unit coupled to the optical sensing unit for determining an optimal location from the plurality of locations based on the detected optical pulses and a pressure sensing unit adapted for detecting a pressure pulse of the user at the optimal location.

In an exemplary embodiment of the present invention, the optical sensing unit comprises at least one optical emitter and a plurality of optical receivers spatially disposed adjacent to the at least one optical emitter.

In another exemplary embodiment, the optical sensing unit is disposed on a different plane to the pressure sensing unit, the optical sensing unit being more proximal to the external surface of the user. In another embodiment, the optical sensing unit is disposed on a same plane as the pressure sensing unit.

In a further embodiment, an external pressure exerted by the device onto the external surface of the user is kept substantially constant during the detection of optical pulses across the plurality of locations.

In another embodiment, the pressure sensing unit is adapted for detecting pressure pulses at the plurality of locations. The optical pulse and the pressure pulse at each location are detected substantially simultaneously and the processing unit determines the optimal location based on the optical pulses and the pressure pulses.

In a further embodiment, the pressure sensing unit further detects an external pressure applied by the device onto the external surface. The device further detects the optical pulse and the pressure pulse at the optimal location for a plurality of the external pressures applied, and determines an optimal external pressure for the blood pressure measurement based on the plurality of optical pulses and the plurality of pressure pulses.

In one embodiment, the device further comprises an actuating unit adapted to actuate the device along the external surface. The processing unit is coupled to the actuating unit for moving the device to the optimal location and for adjusting an external pressure applied by the device.

In yet another embodiment, the optical sensing unit comprises a plurality of optical receivers. The processing unit further assigns a coefficient associated to each optical receiver based on a distance between a location of the optical receiver to the optimal location. The blood pressure is calculated based on the plurality of optical pulses, the coefficients and the pressure pulse.

In another embodiment, a larger coefficient is assigned to the optical receiver for a smaller distance between the optical receiver and the optimal location.

In another aspect of the present invention, a method of measuring a blood pressure of a user using a blood pressure measurement device is disclosed. The method comprises the steps of detecting optical pulses on a plurality of locations on an external surface of the user, determining an optimal location for the blood pressure measurement based on the plurality of optical pulses, detecting a pressure pulse at the optimal location and calculating the blood pressure based on the pressure pulse at the optimal location.

In one embodiment, the method further comprises the steps of determining an optimal external pressure applied by the blood pressure measuring device onto the user, and detecting a pressure pulse and an optical pulse at an optimal condition comprising the optimal location and the optimal external pressure.

In another embodiment, the method further comprises the step of detecting pressure pulses on the plurality of locations. The determining step further determines the optimal location based on the plurality of pressure pulses.

In a further embodiment, the method further comprises the step of determining whether further cuff calibration is needed based on the pressure pulse at the optimal condition, the optimal external pressure and the optical pulse at the optimal condition.

In yet another embodiment, the step of determining whether further cuff calibration is needed comprises the steps: comparing the pressure pulse at the optimal condition against a first threshold; comparing a percentage difference between the optimal external pressure and a reference external pressure against a second threshold; comparing a percentage difference between the optical pulse at the optimal condition and a reference optical pulse against a third threshold; and comparing a ratio of a weighted combined amplitude of the optimal external pressure at the optimal condition and the optical pulse at the optimal condition to a weighted combined amplitude of the reference external pressure and the reference optical pulse against a fourth threshold.

In another embodiment, the calculating step calculates the blood pressure based on the pressure pulse and the optical pulse at the optimal condition, the optimal external pressure, and a plurality of parameters determined from a cuff calibration.

There are many advantages to the present invention. An advantage is that by using an optical sensing unit to locate the artery of the user, the position of the artery is more accurately reflected than a pressure sensing unit, since the pressure signal may diffuse by the tissue under the skin of the user but not the optical signal. By determining the optimal location for the blood pressure measurement, along with the optimal external pressure, the error of calculation of blood pressure is minimized.

Another advantage of the present invention is that the current optimal conditions are compared with the reference conditions to determine whether further cuff calibration is needed. In conventional devices, cuff calibration is needed every time when the device is attached to the user, but the present invention determines certain circumstances that the conditions of the current measurement is sufficiently close to the reference condition such that the cuff calibration is not needed. As such, this invention improves the efficiency of blood pressure measurement in the long run by reducing the number of cuff calibrations needed.

Yet another advantage of the present invention is that the blood pressure can be determined even if the location of measurement is not optimal. The processing unit adjusts the coefficients associated with the optical signals based on the amplitude of the signals for compensation of misalignment of the location of measurement. That means the device does not need to always be attached to the actuating unit or the cuff for measuring blood pressure, thus making the device much more portable.

BRIEF DESCRIPTION OF FIGURES

FIG. 2b is a side view of the blood pressure measurement device of FIG. 2a.

FIG. 5a is an exemplary optical pulse amplitude distribution map, according to an embodiment of the present invention.

FIG. 5b is an exemplary pressure pulse amplitude distribution map, according to an embodiment of the present invention.

FIGS. 6a to 6d are optical pulse amplitude and pressure pulse amplitude distribution maps of a subject under two different external pressures.

FIG. 8a is an exemplary illustrative diagram showing the normalized optical pulse amplitudes associated with each optical receiver for the configuration in FIG. 2a, where the optimal location is aligned to the location of measurement.

FIG. 8b is an exemplary illustrative diagram showing the normalized optical pulse amplitudes associated with each optical receiver for the configuration in FIG. 2a, where the optimal location is not aligned to the location of measurement.

DETAILED DESCRIPTION OF THE PREFERRED EMBODIMENTS

As used herein and in the claims, "comprising" means including the following elements but not excluding others.

As used herein and in the claims, "couple" or "connect" refers to electrical coupling or connection either directly or indirectly via one or more electrical means unless otherwise stated.

Figure 1:
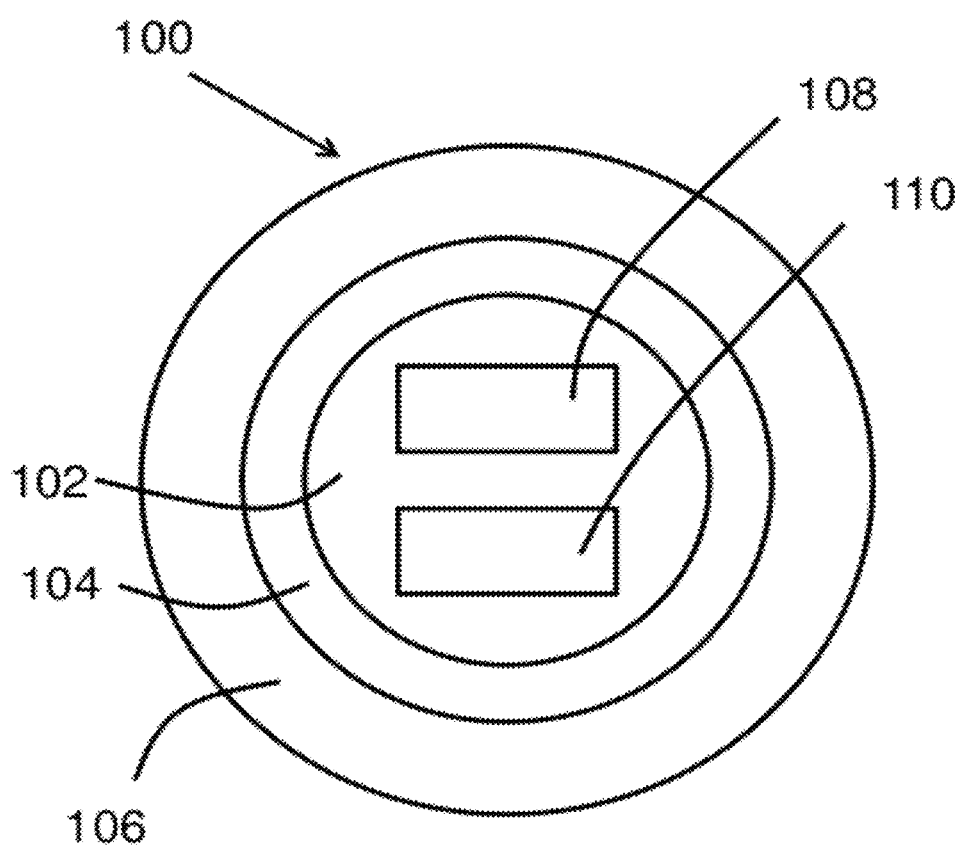
FIG. 1 is a front view of a blood pressure measurement device according to a first embodiment of the present invention.

Referring now to FIG. 1, the first embodiment of the present invention is a blood pressure measuring device 100 including an optical sensing unit 102 or optical sensor disposed on a first surface thereof, a pressure sensing unit 104 provided facing the same first surface as the optical sensing unit 102, and a processing unit 106 coupled to each of the aforementioned components. The optical sensing unit 102 comprises an optical emitter 108 and an optical receiver 110 (or called photo detector). In an embodiment, the optical emitter 108 and the optical receiver 110 are on substantially the same surface with substantially the same orientation. In different embodiments, the pressure sensing unit 104 is either provided on the same plane with the optical sensing unit 102, or is stacked or overlaid on the optical sensing unit 102, as explained in the embodiments below.

Figure 2A:
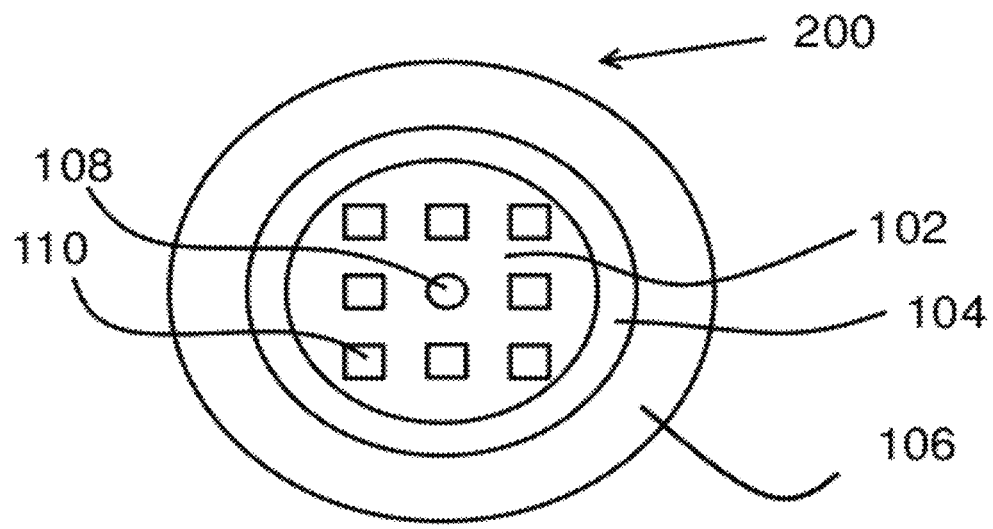
FIG. 2a is a front view of a blood pressure measurement device according to an embodiment of the present invention.
Figure 2B:
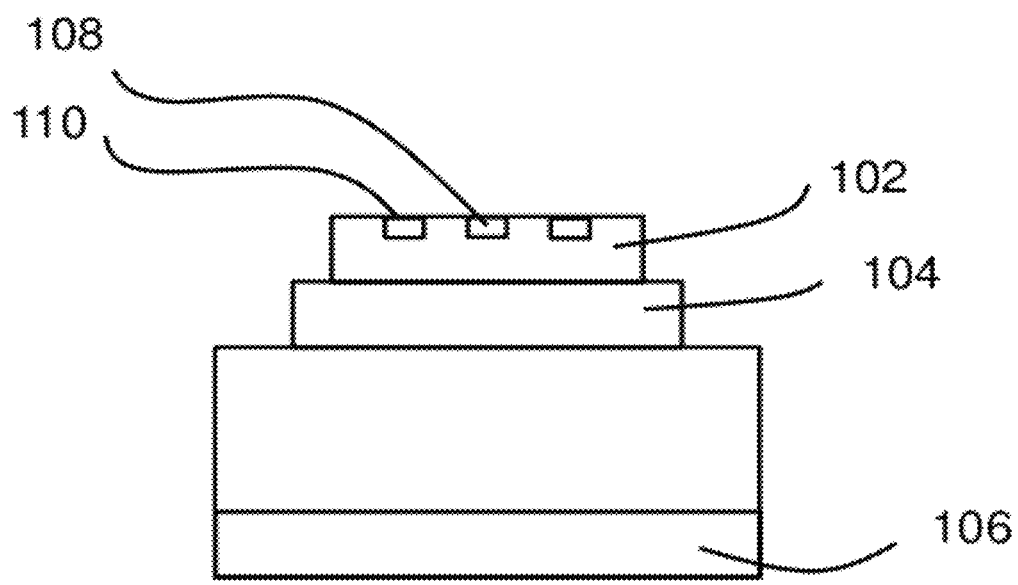
Figure 2C:
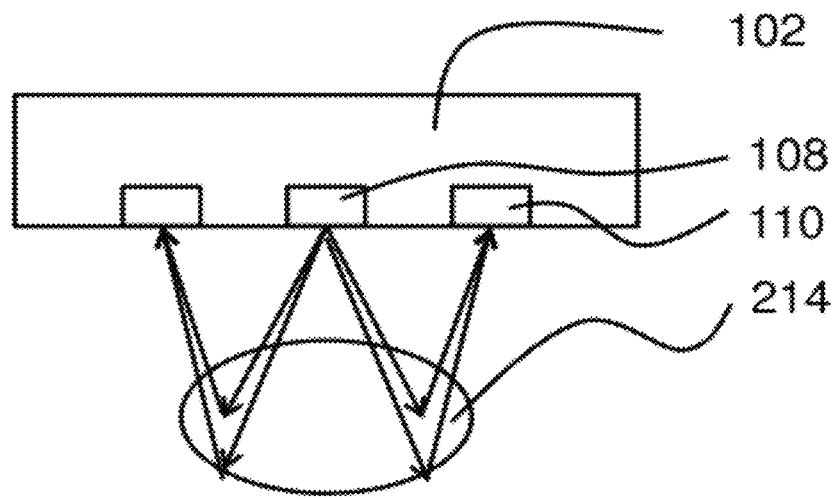
FIG. 2c is an exemplary ray diagram showing the blood pressure measurement device of FIG. 2a receiving reflected light from the artery of the user.
Figure 2D:
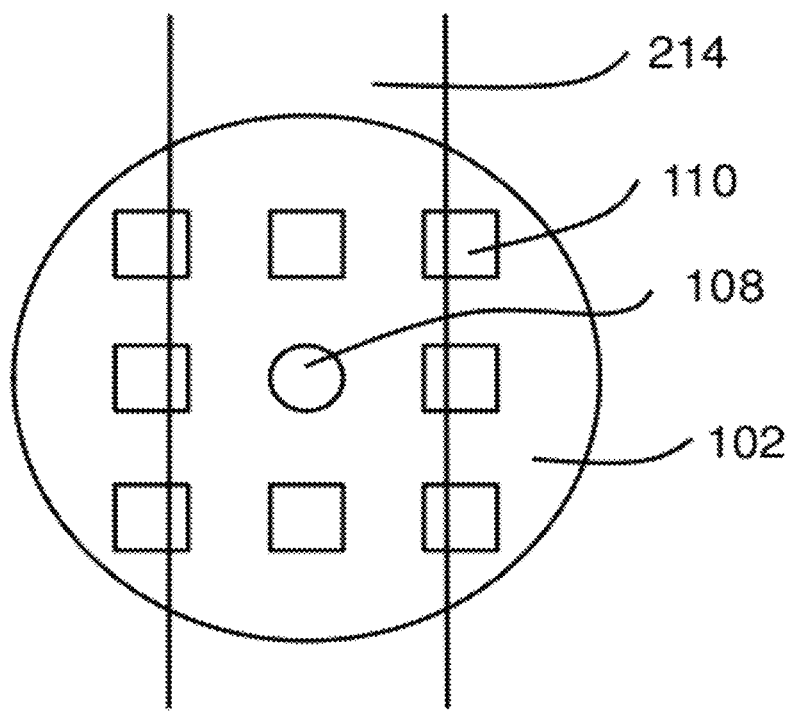
FIG. 2d shows an exemplary arrangement of the blood pressure measurement device of FIG. 2a relative to the artery of the user.

In a specific embodiment as shown in FIGS. 2a and 2b, eight optical receivers 110 are disposed spatially around one optical emitter 108 in a square configuration, functioning as an optical sensor array. The pressure sensing unit 104 is stacked on the optical sensing unit 102, where a substantial area of the pressure sensing unit 104 overlaps with the optical sensing unit 102.

Figure 3:
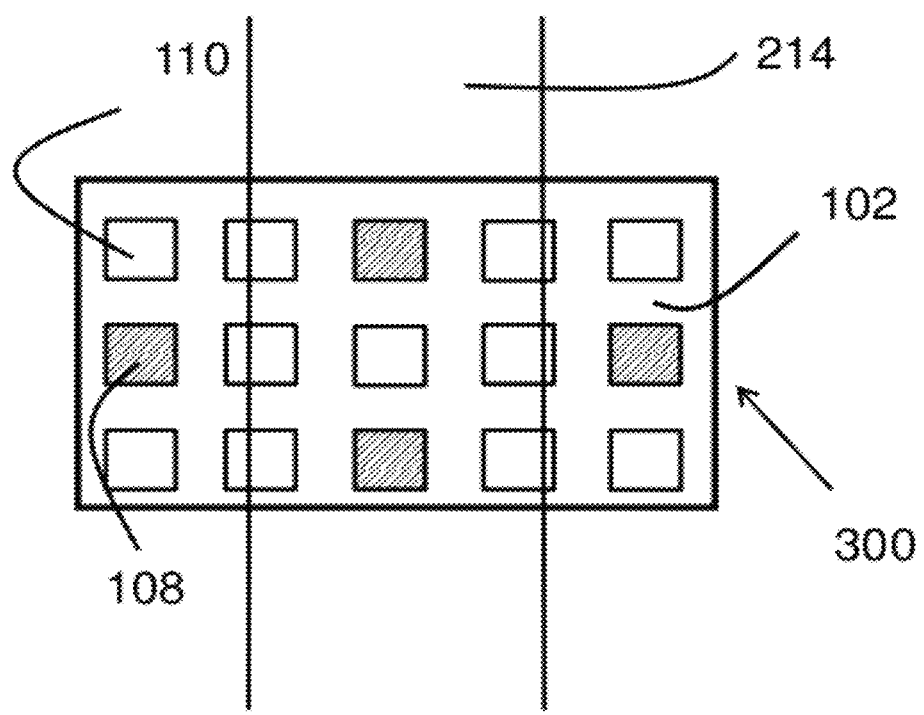
FIG. 3 is a front view of a blood pressure measurement device according to another embodiment of the present invention, with its arrangement relative to the artery.

In another embodiment as shown in FIG. 3, eleven optical receivers 110 i.e. photo detectors are spatially disposed around four optical emitters 108 which are infra-red LEDs. The optical receivers 110 and the optical emitters 108 together form a rectangular two dimensional array, with the four optical emitters 108 forming a diamond configuration. Using multiple optical emitters 108 allows a more accurate detected result due to an increased total power and uniformity of the light emitted. The pressure sensing unit is not shown here for the purposes of illustration, and it is obvious that the pressure sensing unit can be stacked onto or disposed adjacent to the optical sensing unit 102.

Figure 4A:
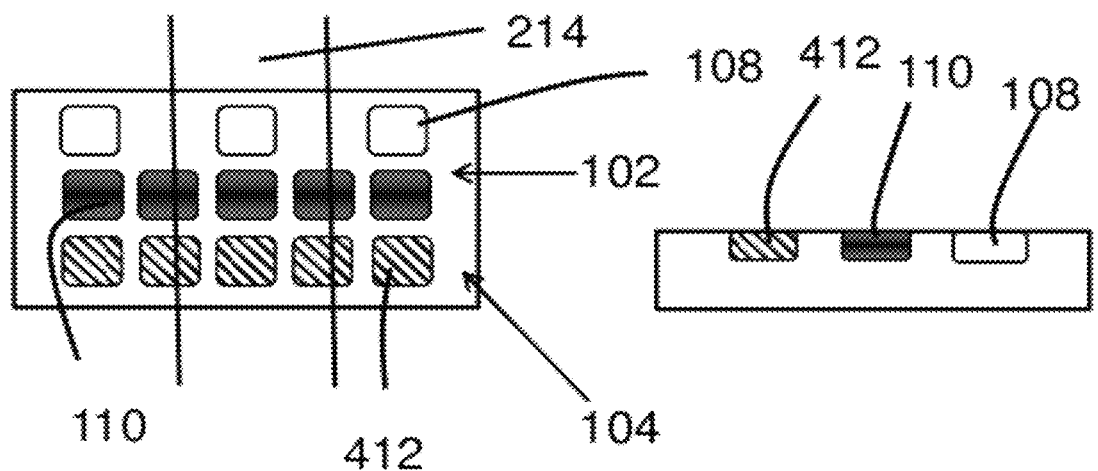
FIGS. 4a and 4b are front views and side views of blood pressure measurement devices according to two other embodiments of the present invention, where the pressure sensing unit is provided at the same plane as the optical sensing unit.
Figure 4B:
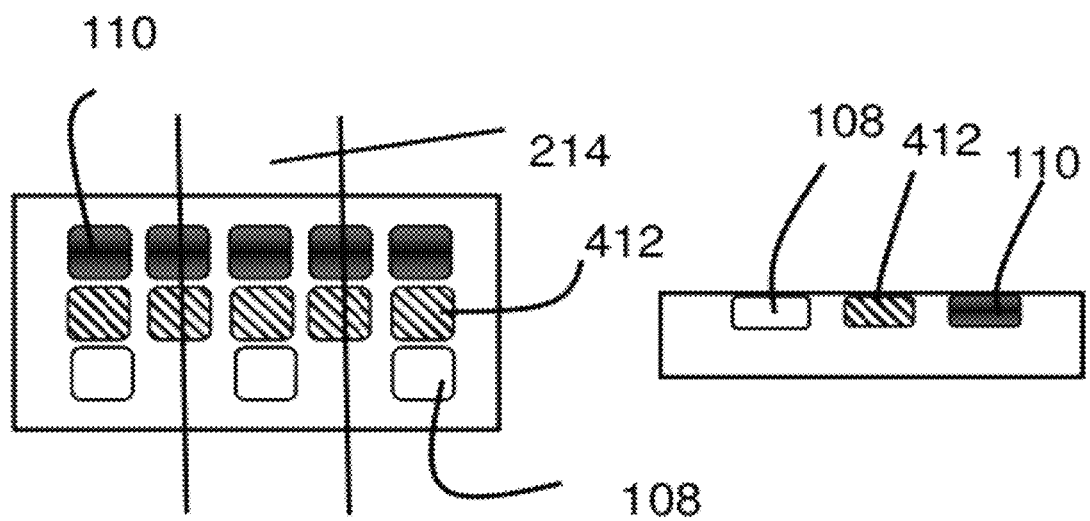

In alternative embodiments as shown in FIGS. 4a and 4b, the pressure sensing unit 104 is provided on the same plane as the optical sensing unit 102. In the embodiment as shown in FIG. 4a, five pressure sensors 412 of the pressure sensing unit 104 are arranged in a linear fashion and disposed immediately adjacent to five optical receivers 110 also arranged in a linear fashion parallel to the pressure sensors 412, while the optical receivers 110 are immediately adjacent to three optical emitters 108 again arranged in a linear fashion parallel to the optical receivers 110 and the optical emitters 108. In the embodiment as shown in FIG. 4b, the five pressure sensors 412 are disposed between the optical emitters 108 and the optical receivers 110. In other words, the optical emitters 108 can be either in the same side or in the opposite side of the optical receivers 110. The working mechanisms of these embodiments are similar to the configurations as in FIGS. 1-3, which will be described in detail below.

However, the number and configuration of optical receivers and emitters are not limited to the current embodiment and can be defined based on different requirements as desired. It is obvious to one skilled in the art that the number and configuration of the optical receivers, optical emitters and pressure sensors can be modified without departing from the scope of the invention. In different embodiments, the optical sensing unit is operable for visible light, infra-red light or a combination thereof.

In an exemplary embodiment, the size of each optical emitter 108 is 1.2×1.2 mm and the size of each optical receiver 110 is 1.2×1.2 mm. There is a distance of 2.54 mm between the optical emitter 108 and an adjacent optical receiver 110 or between two adjacent optical receivers 110. In an exemplary embodiment, the size of each pressure sensor 412 is 2×2 mm. The distance between two adjacent pressure sensors 412 is 2.54 mm.

The optical sensing unit 102 is adapted for detecting an optical pulse or optical signal reflected by the user. Using FIG. 2c as an example, the optical sensing unit functions by using the optical receivers 108 to detect the optical signal emitted by the optical emitter 110 and reflected by an artery 214 of the user, usually a radial artery. The arrows in the figure show the direction of the optical light.

The diameter of human radial artery is normally around 2 mm. The depth of human radial artery located in the wrist is normally 3~5 mm. Thus, the optical sensors not only need to be configured closely enough so that the signal resolution is able to detect the artery location precisely, but also keep the distance between the optical emitter 108 and the optical receiver 110 large enough so that the received signal includes sufficient amount of reflected light from the artery. Feasible range of sizes of the emitter and the receiver: 0.1*0.1 mm~10*10 mm, narrow range of size: 0.1*0.1 mm~4*4 mm. Feasible range of sensor distance: 0 mm~20 mm, narrow range of distance: 2 mm~4 mm.

Besides the blood flowing inside the artery, other tissues under the skin of the user, such as bones or muscle tissues, attenuate light as well. The attenuation by those other tissues is substantially constant while the attenuation of blood is pulsatile due to the blood volume changes caused by cardiac pulsation. Therefore, the amount of light reflected to the optical receiver 110 is pulsatile when the skin is illuminated by the optical emitter 108. The optical pulse is also known as the arterial volume pulse. In an embodiment, the optical pulse received can be divided into a DC component and an AC component. The DC component is related to the other tissues and the AC component is related to the pulsation of the artery. The AC component of the amplitudes of the optical pulse detected by the optical receivers 110 is substantially different between the case where the artery 214 is present and the case where the artery 214 is absent.

In an exemplary embodiment, the device 100 is removably attachable to an actuating unit (not shown). In a further embodiment, the actuating unit is fixable to the wrist of the user. When the actuating unit is fixed to the wrist of the user, and the device 100 is at the attached state, the device 100 is facing towards and contacting the external surface i.e. the skin of the user at around the wrist at the inner side thereof.

In an exemplary embodiment, the actuating unit is movable both transversely and longitudinally on the skin of the user when the device 100 is at the attached position. In a further embodiment, the actuating unit is coupled to the processing unit 108 when the device 100 is at the attached position, and the processing unit 108 controls the movement of the device 100 through the actuating unit.

In operation of the device 100, before measuring the blood pressure of the user, an optimal location for measuring the blood pressure is determined by a locating system as a calibration step. In an exemplary embodiment, the locating system includes the optical sensing unit 102 and the processing unit 106. The optical sensing unit 102 moves on the skin of the user to detect the reflected optical pulse for at least one location on the skin. In one embodiment, the device 100 is attached to the actuating unit such that the processing unit 106 controls the device 100 including the optical sensing unit 102 to move in a predetermined manner once the optical pulse for a location, or called a data point, is detected. In an exemplary embodiment, the optical pulse is detected in 25 different locations on the skin in a 5×5 array, with a 3 mm distance between adjacent data points.

Referring to FIG. 5a, an optical pulse amplitude distribution map of 25 areas on the skin of the user is shown. The distance between adjacent rows and adjacent columns is 3 mm. As shown in the figure, the middle column (column 3) has a substantial difference in the normalized amplitude than the other columns. This result clearly shows that the artery is located substantially along the middle column. Among the 5 data points in the middle column, the center data point (row 3, column 3) has a much larger amplitude than the others. The reason can be that the thickness of the tissue between the skin and the artery of the user is thinnest at the center data point. In an exemplary embodiment, the optimal location is determined to be the area where the amplitude of the optical pulse is the highest.

An external pressure needs to be applied by the device 100 onto the user for the detection of the optical pulses. In an exemplary embodiment, the external pressure is kept substantially constant across the detection for different data points. One reason is that the properties or characteristics of the tissue, such as the density or attenuation characteristics, are dependent to the external pressure applied. In an exemplary embodiment, the processing unit 106 determines and sets the external pressure as necessary by moving the device longitudinally, i.e. towards the skin of the user or away from the skin of the user by controlling the actuating unit. After the external pressure is set, the processing unit 106 controls the actuating unit to move substantially in the transverse plane across the different locations while keeping the external pressure substantially constant. In another embodiment, the external pressure is monitored by the pressure sensing unit 104 and can be adjusted at any location as necessary to keep the external pressure substantially constant.

Figure 9:
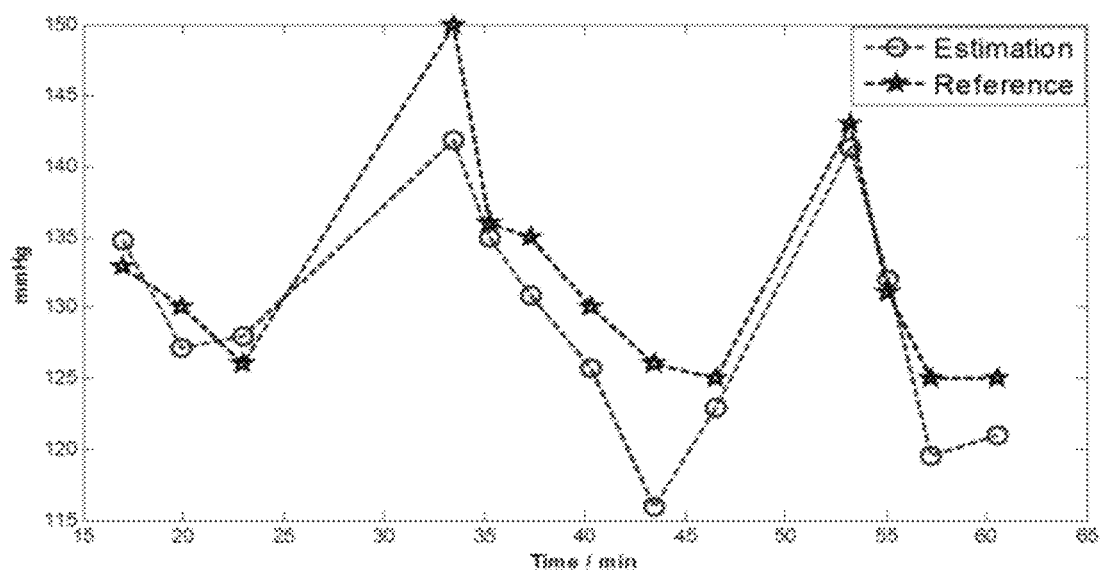
FIG. 9 is a graph showing blood pressures measured using the blood pressure measurement device according to an embodiment of the present invention, and its comparison to cuff calibration measurements.

In an exemplary embodiment, the pressure sensing unit 104 detects a pressure pulse substantially simultaneously to the optical sensing unit 102 detecting the optical pulse. As in the embodiments as shown in FIGS. 1-3, the pressure sensing unit 104 is overlaid on the optical sensing unit 102, with the optical sensing unit 102 more proximal to the skin of the user. The pressure pulse generated at the artery of the user passes through the optical sensing unit 102 and is detected by the pressure sensing unit 104 as the pressure pulse is not substantially blocked or attenuated by the optical sensing unit 102. In the embodiment as shown in FIG. 9, the pressure sensing unit 104 simply detects the pressure pulse directly at the surface of the skin of the user. Although the pressure sensing unit 104 detects the pressure pulse substantially simultaneously to the optical sensing unit 102 detecting the optical pulse in this embodiment, the invention is not so limited and the pressure sensing unit 104 can also function asynchronously with the optical sensing unit 102, as long as the conditions remain sufficiently constant between the detections by the different sensing systems.

In an exemplary embodiment, the pressure pulse is also used along with the optical pulse in determining the optimal location. In general, the optical sensing unit 102 is more accurate in determining the artery position, as the pressure pulse as generated at the artery of the user diffuses more easily than the optical pulse within the tissue of the user. However, even though the artery position is determined, sometimes the pressure pulse, which is the main parameter in calculating the blood pressure, may not be accurately detected. A possible reason is that the artery at that area is not supported by a bone below the artery, therefore the external pressure applied is not fully transmitted to the artery, and in turn the pressure pulse is also not correctly reflected from the detection by the pressure sensing unit 104. In an exemplary embodiment, the amplitude of the pressure pulse for a particular area should be over a predetermined threshold for the area to be considered as the optimal location.

FIG. 5b shows a pressure pulse amplitude distribution map of the 25 data points as in FIG. 5a. Comparing the two distribution maps, it is shown that the two distribution maps both have the largest amplitude along the middle column (column 3). However, the difference between the middle column (column 3) and areas close to the middle column (column 2 and column 4) is not as sharp in the pressure pulse map FIG. 5b as compared to the optical pulse map FIG. 5a. Further, the amplitude of the pressure pulse at the center data point (row 3, column 3) in the pressure pulse map FIG. 5b is not the highest where the amplitude of the optical pulse in the optical pulse map FIG. 5a is the highest. These findings are consistent with the description in the previous paragraphs.

FIGS. 6a to 6d shows the optical pulse and pressure pulse amplitudes detected under two different external pressures at the same location. More specifically, the data in FIGS. 6a and 6b are detected under a higher external pressure than FIGS. 6c and 6d. FIG. 6a and FIG. 6c are the optical pulse amplitude maps and FIG. 6b and FIG. 6d are the pressure pulse amplitude maps. As shown in FIGS. 6a and 6c, the largest amplitude of the optical pulse are both at the center data point (row 3, column 3), therefore the center area can be determined as the optimal location. By comparison with the pressure pulse maps (FIG. 6b and FIG. 6d), the optical pulse maps (FIGS. 6a and 6c) have a more substantial difference between the optimal location (center data point) and the other locations (surrounding data points) in general, meaning the optical signal is more sensitive than the pressure signal. Particularly, in FIG. 6d, there are multiple surrounding data points where the pressure pulses detected are stronger than the pressure pulse detected at the center data point. For the purposes of determining the optimal location for blood pressure measurement, the data shown in FIGS. 6a and 6b is more preferred than the data as shown in FIGS. 6c and 6d, due to the more evenly distributed pressure pulse amplitudes and the higher external pressure applied for FIGS. 6a and 6b.

A single pressure sensing unit 104 can simultaneously detect the external pressure and also the pressure pulse. The reason is that the external pressure is kept substantially constant, and there are data points where the pressure pulse is completely non-existent, so the processing unit 106 can easily separate the two pressure components. In other words, the DC component of the detected pressure signal is the external pressure, while the AC component of the pressure signal is the pressure pulse.

In a further embodiment of the present invention, after the optimal location for measuring blood pressure is determined, the optimal external pressure is also determined for calibration. At the optimal location, at least one optical pulse and pressure pulse is detected while the external pressure applied is varied in a predetermined range. When measuring blood pressure of the user, a part of the artery should be flattened by the external pressure applied by the device 100. If the external pressure is too low, the artery would not be flattened by the external pressure, and the pressure pulse may be too weak that cannot be fully detected by the pressure sensing unit 104. On the other hand, if the external pressure is too high, the artery will be occluded by the external pressure, and will in turn affect the pressure pulse when blood flows through the artery. In general, the detected pressure pulse amplitude will be increased to get a maximum value when the external pressure is increased from zero; and after achieving the maximum amplitude, a heavier external pressure will result in a smaller detected pressure pulse amplitude. If the external pressure is so heavy that it totally occludes the artery, there will be no pressure pulse at all.

Figure 7:
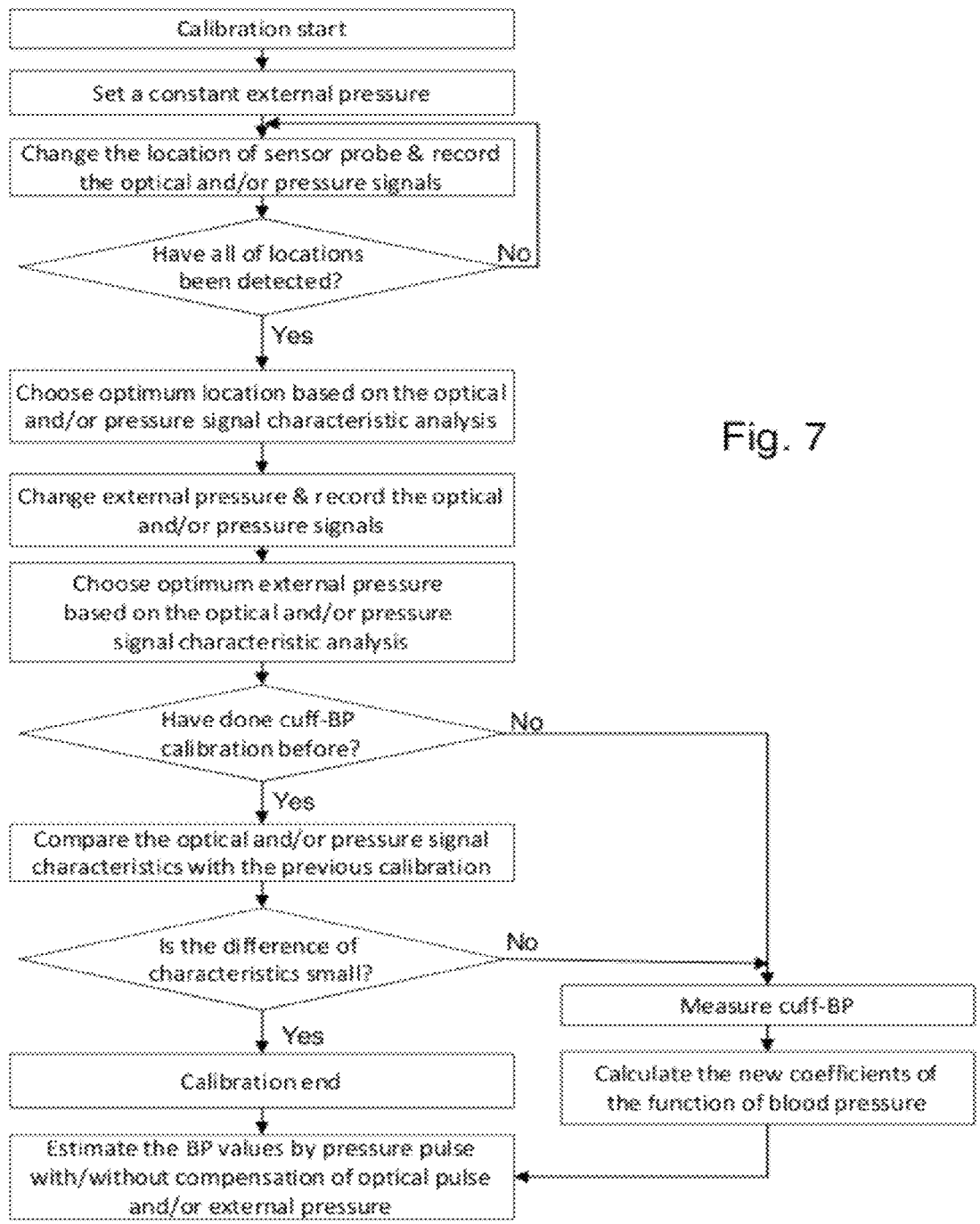
FIG. 7 is flow chart for dynamic calibration procedures of a blood pressure measurement device according to an embodiment of the present invention.

In an exemplary embodiment, a flow chart of a dynamic calibration procedure of a blood pressure measurement device is shown as FIG. 7. First, the external pressure is set at a constant value as described above, but the value does not need to be optimal. Then, the device is moved across different locations on the external surface of the user for detecting the optical signal (with or without pressure signal) at each location. The characteristics of the optical signal and the pressure signal are then analyzed for determining the optimum location for taking the measurement. The characteristics include but are not limited to: amplitude, rise time, fall time, ratio of rise time to fall time, first derivative with characteristic points thereof, and second derivative with characteristic points thereof. At the optimum location, multiple optical signals and pressure signals are taken at different external pressures. The signals are then analyzed, using the same characteristics as above, to determine the optimal external pressure for taking the measurement. After the optimal location and external pressure are obtained, the device then checks whether a previous cuff calibration has been performed for this device. If a previous cuff calibration has been performed, then the optical and pressure signals are compared to the previous cuff calibration data stored in the device 100. In cases where a previous calibration has not been performed, or the current optical and pressure signals are sufficiently different from the previous cuff calibration data, a cuff calibration needs to be performed for updating the settings and parameters for the device. The user will be informed if a new cuff calibration is needed. After the calibration, or if calibration is not needed, the blood pressure of the subject is estimated by the pressure pulse.

The above steps are performed for the first use of the blood pressure measurement device, or at a time where the device is re-attached to the user for measurement. In an exemplary embodiment, for the first time of calibration, the device 100 moves on the skin of the user to determine the optimal location of measuring blood pressure as mentioned above. For the single optical sensing unit 102, the optimum location is defined as the position where maximum optical pulsation amplitudes are recorded. For the configuration of the eight optical receivers 110 as shown in FIG. 2a, the approximate normalized optical pulse amplitude is as shown in FIG. 8a. The amplitudes decrease with the distance between sensing location and optimal location increases. In this mode, as the area of measurement is aligned to the optimal location, the amplitudes are symmetric with respect to the center of the area. As shown in FIG. 8a, the amplitude associated with the four optical receivers 110 directly adjacent to the optical emitter 108 at the center is 0.15, while the amplitude associated with the four corner optical receivers 110 is 0.10, since the corner optical receivers 110 are farther away from the optical emitter 108, which is the optimal location.

After determining the optimal location, the device 100 is moved to this optimal location and the external pressure is varied in the pre-determined range where multiple measurements on optical signal and pressure signal are taken. The optimum external pressure depends on whether both pressure and optical pulses are reasonably large enough. The characteristics of pressure pulse and/or optical pulse at optimal location and under optimal external pressure, for example those as listed above, are recorded for recalibration procedures. After that, a standard BP measurement is processed by using a cuff BP machine. The readings of systolic and/or diastolic BP are recorded. The parameters for calculating the blood pressure is determined through the cuff calibration, as described below.

In an exemplary embodiment, when the device 100 is re-attached to the user through the actuating unit, the calibration procedures of optimal location and optimal external pressure as mentioned above are re-approached. The characteristics of current pressure and/or optical pulses at optimal location and under optimal external pressure are compared with the previous ones. If the differences of those characteristics are small, cuff calibration procedures are waived. Otherwise, new cuff calibration procedures are needed.

In an exemplary embodiment, the comparison of current and previous characteristics of pressure and/or optical pulses at optimal location and under optimal external pressure is performed on 4 different values. First, the current pressure pulse amplitude should be larger than a first threshold, i.e. PP>A. Second, the percentage difference between the current external pressure and the previous external pressure should be smaller than a second threshold, i.e. $(EP-EP_0)/EP_0<B$. Third, the percentage difference between the current optical pulse amplitude and the previous optical pulse amplitude should be smaller than a third threshold, i.e. $(OP-OP_0)/OP_0<C$. Lastly, the ratio of a weighted combined amplitude of the external pressure and the optical pulse should be smaller than a fourth threshold, i.e. $(\mu \times EP+OP)/(\mu \times EP_0+OP_0)<D$. If all of above conditions are satisfied, cuff calibration procedures are waived. Otherwise, new cuff calibration procedures are needed.

In another embodiment, a static calibration procedure is provided as an alternate to the dynamic calibration procedure described above. For example, the device 200 does not need to be attached to the actuating unit, and the location of measurement does not need to be aligned to the optimal location. Rather, any misalignment between the location of measurement and the optimal location is compensated by the processing unit 106 based on the normalized amplitudes of the optical pulses of different locations.

In an example as shown in FIG. 8b, the area at the right to the center has a value of 0.20, and in general the right column has a larger normalized amplitude and the left column has a reduced normalized amplitude. It can then be determined that the area with the 0.20 normalized amplitude is the optimal location. The center of the device 200 is slightly off-aligned so that the pressure pulse measured by pressure sensor is smaller than that measured at the optimal location. An adjustment of blood pressure calculation, e.g., increasing the coefficient of pressure pulse, will be determined by the processing unit 106.

In an embodiment, the comparison mentioned above is first conducted to determine whether cuff calibration is needed. If cuff calibration is not needed, then the operation mode is chosen between dynamic calibration and static calibration. If static calibration is chosen, then the optimal location is determined and compensation is calculated by the processing unit 106. It can be assumed that the device 200 is placed sufficiently close to the optimal location such that the optimal location exists at an area which can be detected by an optical receiver, where multiple optical receivers are present. If dynamic calibration is chosen, the device 200 then needs to be moved to the optimal location, either through the actuating unit or manually. In other words, dynamic mode moves the location of measurement to the optimal location, while static mode compensates the misalignment by algorithms stored in processing unit 106.

The blood pressure (BP), e.g., systolic BP, diastolic BP and/or mean BP, is calculated by using the pressure pulse. The optical pulse, and/or the direct current part of the optical signal and/or the external pressure can also be used as the compensation parameters of blood pressure calculation.

In an exemplary embodiment, the blood pressure (BP) of the user is calculated by an equation of BP=a+b*PP, where a and b are predetermined parameters obtained from a cuff calibration procedure, PP is the amplitude of the pressure pulse.

In another embodiment, the blood pressure (BP) of the user is calculated by an equation of BP=a+b*PP+d*OP+e*OD, where a, b, d and e are predetermined parameters obtained from a cuff calibration procedure, PP is the amplitude of the pressure pulse, OP is the amplitude of the optical pulse and OD is the amplitude of the direct current part of the optical signal.

In a further embodiment, the blood pressure (BP) of the user is calculated by an equation of BP=a+b*PP+c*EP+d*OP+e*OD, where a, b, c, d, and e are predetermined parameters obtained from a cuff calibration procedure, PP is the amplitude of the pressure pulse, EP is the external pressure, OP is the amplitude of the optical pulse and OD is the amplitude of the direct current part of the optical signal.

All of the formulas described in previous 3 paragraphs could be more complex. Multiple pressure signals and/or multiple optical signals could be used for blood pressure calculation. Moreover, the formulas are not limited to linear equations. Non-linear calculation, e.g., neural-network (fuzzy logic) calculation could be included. In general, the BP is expressed by a function of PP, EP, OP and/or OD as $$BP=f(PP_1, \ldots, PP_m, EP_1, \ldots, EP_n, OP_1, \ldots, OP_i, OD_1, \ldots, OD_j).$$

In an exemplary embodiment, the cuff calibration is performed based on a plurality of reference points. The optical pulse, pressure pulse and external pressure are collected for these reference points, and the blood pressures as measured using a conventional cuff are also collected. Based on these data, predetermined parameters, i.e. a-e as in the above examples, are calculated to fit the reference blood pressure readings and then used to the measured blood pressure. In a specific embodiment as shown in FIG. 9, a number of blood pressure measurements are taken after these predetermined parameters are given. In a 60-minute period of exercise-recovery repetitions, the discrepancy between the calculated blood pressure and the cuff-based reference is only −3.0±3.6 mmHg.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A method of operating a blood pressure measurement device adapted for measuring blood pressure on an external surface of a user, comprising the steps of:
   a) determining an optimal location for calculating said blood pressure by a processing unit of said device based on a plurality of optical pulses and a plurality of pressure pulses obtained from an optical sensing unit and a pressure sensing unit of said device substantially simultaneously while applying a first constant external pressure by controlling an actuating unit of said device;

b) performing a cuff calibration to obtain parameters for said blood pressure calculation by said processing unit;

c) calculating said blood pressure based on an optical pulse, a pressure pulse and an optimal external pressure measured at a location of measurement which is aligned to said optimal location and said parameters for said blood pressure calculation by said processing unit, and d) determining whether further cuff calibration is needed based on said pressure pulse at said location of measurement, said optimal external pressure and said optical pulse at said location of measurement by:
   (1) comparing said pressure pulse at said location of measurement against a first threshold;
   (2) comparing a percentage difference between said optimal external pressure and a reference external pressure against a second threshold;
   (3) comparing a percentage difference between said optical pulse at said location of measurement and a reference optical pulse against a third threshold;
   (4) comparing a ratio of a weighted combined amplitude of said optimal external pressure and said optical pulse at said location of measurement to a weighted combined amplitude of said reference external pressure and said reference optical pulse against a fourth threshold; and
   (5) waiving said further cuff calibration if
      i. said pressure pulse at said location of measurement is larger than said first threshold,
      ii. said percentage difference between said optimal external pressure and said reference external pressure is less than said second threshold,
      iii. said percentage difference between said optical pulse at said location of measurement and said reference optical pulse is less than said third threshold, and
      iv. said ratio of weighted combined amplitude of said optimal external pressure and said optical pulse at said location of measurement to said weighted combined amplitude of said reference external pressure and said reference optical pulse is less than said fourth threshold.

2. The method according to claim 1, further comprising the step of determining whether said location of measurement is aligned to said optimal location.

3. The method according to claim 1, wherein said calculating step further comprises the step of adjusting a coefficient associated to said optical pulse at said location of measurement to compensate misalignment of said location of measure to said optimal location when said processing unit determines said location of measurement is not aligned to said optimal location.

4. The method according to claim 3, wherein said coefficient associated to said optical pulse is determined by cuff calibration.

5. The method according to claim 1, wherein said step of determining said optimal location for calculating said blood pressure further comprises the steps of
a) setting said actuating unit of said device to control said device to apply said first constant external pressure on said external surface across a plurality of locations;
b) obtaining said optical pulses at said plurality of locations from said optical sensing unit of said device and substantially simultaneously obtaining said pressure pulses at said plurality of locations from said pressure sensing unit of said device;
c) locating a location of interest that is corresponded to the highest amplitude optical pulse among said obtained optical pulses by said processing unit;
d) determining if said location of interest has a corresponding pressure pulse over a predetermined value by said processing unit;
e) setting said location of interest as said optimal location if said corresponding pressure pulse is over said predetermined value by said processing unit.

6. The method according to claim 1, further comprising the steps of applying a plurality of different external pressures onto said external surface at said optimal location by said actuating unit; and further detecting an additional optical pulse and an additional pressure pulse at said optimal location for each of said plurality of different external pressures applied, and determines said optimal external pressure for said blood pressure measurement based on said additional optical pulses and said additional pressure pulses, wherein said optimal external pressure is one of said plurality of different external pressures applied at said optimal location at which said additional optical pulse is greater than a first predetermined threshold value and said additional pressure pulse is greater than a second predetermined threshold value.

7. A method of operating a blood pressure measurement device, comprising the steps of:
a) detecting a plurality of optical pulses on an external surface of a user by an optical sensing unit of said device;
b) determining an optimal condition for said blood pressure measurement based on said plurality of optical pulses;
c) detecting a pressure pulse at a location of measurement by a pressure sensing unit of said device; and
d) calculating said blood pressure based on said pressure pulse and said optimal condition,
wherein said step of determining said optimal condition comprises the steps of:
(1) determining an optimal location based on said optical pulses measured at a plurality of locations of said external surface of said user, and
(2) determining said optimal location based on said plurality of pressure pulses,
wherein the method of operating a blood pressure measurement device further comprises the step of determining whether cuff calibration is needed based on said pressure pulse at said location of measurement, an optimal external pressure and said optical pulse at said location of measurement, and said step of determining whether cuff calibration is needed comprises the steps of:
(1) comparing said pressure pulse at said location of measurement against a first threshold;
(2) comparing a percentage difference between said optimal external pressure and a reference external pressure against a second threshold;
(3) comparing a percentage difference between said optical pulse at said location of measurement and a reference optical pulse against a third threshold; and
(4) comparing a ratio of a weighted combined amplitude of said optimal external pressure and said optical pulse at said location of measurement to a weighted combined amplitude of said reference external pressure and said reference optical pulse against a fourth threshold; and
(5) waiving said cuff calibration if:
   i. said pressure pulse at said location of measurement is larger than said first threshold,
   ii. said percentage difference between said optimal external pressure and said reference external pressure is less than said second threshold, iii. said percentage difference between said optical pulse at said location of measurement and said reference optical pulse is less than said third threshold, and iv. said ratio of weighted combined amplitude of said optimal external pressure and said optical pulse at said location of measurement to said weighted combined amplitude of said reference external pressure and said reference optical pulse is less than said fourth threshold.

8. A blood pressure measurement device adapted for measuring blood pressure at an external surface of a user, comprising:
   a) an optical sensing unit adapted for detecting an optical pulse at each of a plurality of locations on said external surface of said user;
   b) an actuating unit adapted for actuating said device to move along said external surface and apply a plurality of different external pressures onto said external surface;
   c) a pressure sensing unit adapted for detecting a pressure pulse of said user at each of said plurality of locations; and
   d) a processing unit coupled to said optical sensing unit, said actuating unit and said pressure sensing unit,
   wherein said processing unit is adapted for determining an optimal location for said device to measure said blood pressure by:
      (1) setting said actuating unit to control said device to apply a first external pressure onto said external surface across said plurality of locations, wherein said first external pressure is constant;
      (2) obtaining said optical pulse at each of said plurality of locations from said optical sensing unit and substantially simultaneously obtaining said pressure pulse at each of said plurality of locations from said pressure sensing unit;
      (3) locating a location of interest that is corresponded to the highest amplitude optical pulse among said obtained optical pulses;
      (4) determining if said location of interest has a corresponding pressure pulse over a predetermined value; and
      (5) setting said location of interest as said optimal location if said corresponding pressure pulse is over said predetermined value,
   wherein said device is adapted for measuring said blood pressure at a location of measurement which is aligned to said optimal location,
   wherein said processing unit is further adapted for determining whether cuff calibration is needed based on said pressure pulse at said location of measurement, an optimal external pressure and an optical pulse at said location of measurement, wherein said step of determining whether cuff calibration is needed comprises the steps of:
      (1) comparing said pressure pulse at said location of measurement against a first threshold;
      (2) comparing a percentage difference between said optimal external pressure and a reference external pressure against a second threshold;
      (3) comparing a percentage difference between said optical pulse at said location of measurement and a reference optical pulse against a third threshold; and
      (4) comparing a ratio of a weighted combined amplitude of said optimal external pressure and said optical pulse at said location of measurement to a weighted combined amplitude of said reference external pressure and said reference optical pulse against a fourth threshold; and
   (5) waiving said cuff calibration if:
      i. said pressure pulse at said location of measurement is larger than said first threshold,
      ii. said percentage difference between said optimal external pressure and said reference external pressure is less than said second threshold,
      iii. said percentage difference between said optical pulse at said location of measurement and said reference optical pulse is less than said third threshold, and
      iv. said ratio of weighed combined amplitude of said optimal external pressure and said optical pulse at said location of measurement to said weighted combined amplitude of said reference external pressure and said reference optical pulse is less than said fourth threshold.

9. The device according to claim 8, wherein said optical sensing unit comprises at least one optical emitter and at least one optical receiver spatially disposed adjacent to said at least one optical emitter.

10. The device according to claim 8, wherein said optical sensing unit is disposed on a different plane to said pressure sensing unit, said optical sensing unit being more proximal to said external surface of said user.

11. The device according to claim 8, wherein said optical sensing unit is disposed on a same plane as said pressure sensing unit.

12. The device according to claim 8, wherein said processing unit determines whether said location of measurement is aligned to said optimal location.

13. The device according to claim 12, wherein said processing unit adjusts a coefficient associated to said optical pulse at said location of measurement to compensate misalignment of said location of measure to said optimal location when said processing unit determines said location of measurement is not aligned to said optimal location.

14. The device according to claim 8, wherein said processing unit is further adapted for
   a) performing a cuff calibration to obtain parameters for a blood pressure calculation; and
   b) calculating said blood pressure based on an optical pulse, a pressure pulse and an optimal external pressure measured at said location of measurement which is aligned to said optimal location and said parameters for blood pressure calculation.

15. The device according to claim 14, wherein said pressure sensing unit further detects said plurality of different external pressure applied by said device onto said external surface, said device further detects an additional optical pulse and an additional pressure pulse at said optimal location for each of said plurality of different external pressures applied, and determines said optimal external pressure for said blood pressure measurement based on said additional optical pulses and said additional pressure pulses, wherein said optimal external pressure is one of said plurality of different external pressures applied at said optimal location at which said additional optical pulse is greater than a first predetermined threshold value and said additional pressure pulse is greater than a second predetermined threshold value.

* * * * *